United States Patent

Roesler et al.

[11] Patent Number: 5,908,948
[45] Date of Patent: Jun. 1, 1999

[54] COMPOUNDS CONTAINING UREA AND ALKOXYSILANE GROUPS

[75] Inventors: Richard R. Roesler, Wexford; Edward P. Squiller, Pittsburgh, both of Pa.; Philip E. Yeske, Cologne, Germany; Stanley F. Siranovich, Imperial, Pa.

[73] Assignee: Bayer Corporation, Pittsburgh, Pa.

[21] Appl. No.: 08/814,561

[22] Filed: Mar. 11, 1997

[51] Int. Cl.⁶ ........................................................ C07F 7/10
[52] U.S. Cl. ............................ 556/421; 544/216; 544/221; 544/222; 528/18
[58] Field of Search ............................. 556/421; 544/216, 544/221, 222; 528/18

[56] References Cited

U.S. PATENT DOCUMENTS

| | | | |
|---|---|---|---|
| 2,832,754 | 4/1958 | Kenmore et al. | 260/46.5 |
| 2,971,864 | 2/1961 | Speier | 117/124 |
| 3,676,478 | 7/1972 | Golitz et al. | 260/448.2 N |
| 4,481,364 | 11/1984 | Chu et al. | 556/413 |
| 5,126,170 | 6/1992 | Zwiener et al. | 427/385.5 |
| 5,236,741 | 8/1993 | Zwiener et al. | 427/385.5 |
| 5,312,943 | 5/1994 | Gaglani | 556/421 X |
| 5,364,955 | 11/1994 | Zwiener et al. | 556/418 |
| 5,523,443 | 6/1996 | Gaglani | 556/421 |
| 5,532,398 | 7/1996 | Wolter et al. | 556/421 X |
| 5,550,272 | 8/1996 | Lewis et al. | 556/421 X |
| 5,554,709 | 9/1996 | Emmerling et al. | 528/27 |

FOREIGN PATENT DOCUMENTS

| | | |
|---|---|---|
| 1243189 | 8/1971 | United Kingdom . |
| 1243190 | 8/1971 | United Kingdom . |

OTHER PUBLICATIONS

Angew. Chem. 98, 1986, pp. 237–253.

*Primary Examiner*—Paul F. Shaver
*Attorney, Agent, or Firm*—Joseph C. Gil; Thomas W. Roy

[57] ABSTRACT

The present invention relates to compounds containing alkoxysilane and urea groups corresponding to the formula

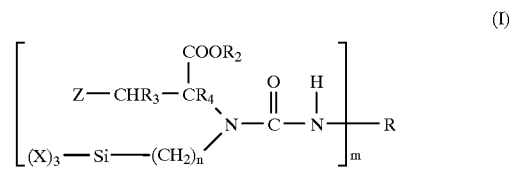

(I)

wherein

X represents identical or different organic groups which are inert to isocyanate groups below 100° C., provided that at least one of these groups is an alkoxy group, Z represents $COOR_1$ or an aromatic ring, R represents the residue obtained by removing the isocyanate groups from an organic monomeric polyisocyanate or a polyisocyanate adduct, $R_1$ and $R_2$ are identical or different and represent organic groups which are inert to isocyanate groups at a temperature of 100° C. or less, $R_3$ and $R_4$ are identical or different and represent hydrogen or organic groups which are inert to isocyanate groups at a temperature of 100° C. or less and n is an integer from 1 to 8.

The present invention also relates to the use of these compounds for the preparation of coatings, sealants and adhesives.

13 Claims, No Drawings

COMPOUNDS CONTAINING UREA AND ALKOXYSILANE GROUPS

BACKGROUND OF THE INVENTION

1. Field of the Invention

The present invention relates to new compounds containing alkoxysilane groups and urea groups and to their use as coatings, sealants, or adhesives.

2. Description of the Prior Art

Hydrolyzable organofunctional silanes are key components for linking conventional polymer chemistry with silicone chemistry. Compounds of technical importance for this purpose are in particular those corresponding to the formula $$(RO)_3Si—(CH_2)_3—Y$$

wherein
R is an alkyl group and
Y is a functional group.

Such compounds contain both hydrolyzable silyl groups, OR, which crosslink by "silane polycondensation" in the presence of moisture, and other functional groups, Y, which enable them to be chemically linked to conventional polymer materials. (See e.g., *Angew. Chem.* 98 (1986) 237–253.)

Hydrolyzable functional silanes corresponding to the above formula in which the functional group Y contains Zerewitinoff active H-atoms are potentially capable of modifying polyisocyanates. (See, e.g., WO 92/05212). Commercially available products suitable for this purpose contain $NH_2$ and/or NH groups as Zerewitinoff active H-atoms. Also available are compounds containing SH groups.

Alkoxysilanes containing SH groups are described, for example, in GB-A-1,102,251; EP-A-0,018,094; DE-A-1,162,818; U.S. Pat. No. 3,590,065; U.S. Pat. No. 3,849,471; U.S. Pat. No. 4,082,790; U.S. Pat. No. 4,012,403; and U.S. Pat. No. 4,401,286. All alkoxysilanes containing SH groups have the unpleasant odor which is typical of mercaptans. The polymer may, therefore, have an unpleasant odor due to residues of these compounds.

α-Aminoalkyl silane derivatives which can be crosslinked by moisture may be prepared according to German Offenlegungsschriften Nos. 1,812,504 and 1,812,562. The functional silanes described there have, however, failed to achieve technical importance due to the complicated process for their synthesis.

Alkoxysilanes containing amino groups are described, e.g., in *J. Org. Chem.* 36 (1971), p. 3120; DE-A-1,152,695; DE-A-1,271,712; DE-A-2,161,716; DE-A-2,408,480; DE-A-2,521,399; DE-A-2,749,316; U.S. Pat. No. 2,832,754; U.S. Pat. No. 2,971,864; and U.S. Pat. No. 4,481,364. Common to all amino-functional silanes known in the art is the disadvantage of being extremely reactive with isocyanates. Therefore, it is difficult to react these alkoxysilanes with polyisocyanates due to the incompatibility, inhomogeneity and extremely high viscosities of the reaction products.

U.S. Pat. No. 5,554,709 discloses that amino-functional silanes can be reacted with certain NCO prepolymers, provided that the functionality of the prepolymer is less than 2.

U.S. Pat. No. 5,364,955 discloses that by initially reacting amino-functional silanes with maleic or fumaric acid esters to form secondary amino groups (i.e., aspartates), it is then possible to react these aspartates with NCO prepolymers without encountering incompatibility, inhomogeneity or extremely high viscosities in the reaction products. However, this reference does not disclose that it is possible to react all types of polyisocyanates with aspartates, i.e., polyisocyanate monomers and polyisocyanate adducts are not disclosed.

It is an object of the present invention to provide compounds containing urea and alkoxysilane groups that are either liquid or capable of being dissolved in commonly used organic solvents, are based on polyisocyanate monomers and/or polyisocyanate adducts, and do not suffer from the incompatibility, inhomogeneity and viscosity problems encountered with the prior art reaction products of isocyanates with alkoxysilanes containing NH groups. It is an additional object of the present invention to provide compounds containing alkoxysilane groups that can be cured by silane polycondensation to form coatings, sealants, and adhesives.

These objects may be achieved with the compounds containing alkoxysilane groups and urea groups according to the present invention described hereinafter. These compounds are prepared by reacting polyisocyanate monomers and/or adducts with aspartates (obtained by reacting aminoalkyl alkoxysilanes with maleic or fumaric acid esters) to form compounds containing urea groups.

It is surprising that the products according to the invention are liquid at room temperature because the corresponding products prepared by the direct reaction of polyisocyanate monomers and/or adducts with aminoalkyl alkoxysilanes are solids that cannot be dissolved with conventional coating solvents. The prior art, i.e., U.S. Pat. Nos. 5,554,709 and 5,364,955, only teaches that the reaction product of an NCO prepolymer with either an aminoalkyl alkoxysilane or an aspartate prepared from an aminoalkyl alkoxy silane is liquid. It does teach that it would be possible to convert the solid reaction products prepared from polyisocyanate monomer and/or adducts to liquid products by using the aspartate form of the aminoalkyl alkoxysilanes.

SUMMARY OF THE INVENTION

The present invention relates to compounds containing alkoxysilane and urea groups corresponding to the formula

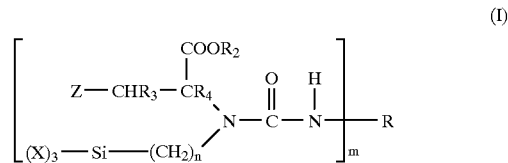

(I)

wherein
X represents identical or different organic groups which are inert to isocyanate groups below 100° C., provided that at least one of these groups is an alkoxy group,
Z represents $COOR_1$ or an aromatic ring,
R represents the residue obtained by removing the isocyanate groups from an organic monomeric polyisocyanate or a polyisocyanate adduct,
$R_1$ and $R_2$ are identical or different and represent organic groups which are inert to isocyanate groups at a temperature of 100° C. or less,
$R_3$ and $R_4$ are identical or different and represent hydrogen or organic groups which are inert to isocyanate groups at a temperature of 100° C. or less and
n is an integer from 1 to 8.

The present invention also relates to the use of these compounds for the preparation of coatings, sealants and adhesives.

DETAILED DESCRIPTION OF THE INVENTION

The compounds containing alkoxysilane groups and urea groups of formula I are prepared by reacting polyisocyanate monomers and/or adducts with compounds containing alkoxysilane and aspartate groups (secondary amino groups) corresponding to the formula

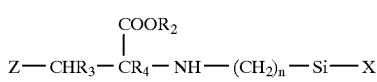 (II)

to form compounds containing alkoxysilane and urea groups.

The compounds of formula II are prepared by reacting aminoalkyl alkoxysilanes corresponding to the formula

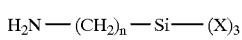 (III)

with maleic, fumaric or cinnamic acid esters corresponding to the formula

 (IV)

In formulas I to IV

X represents identical or different organic groups which are inert to isocyanate groups below 100° C., provided that at least one of these groups is an alkoxy group, preferably alkyl or alkoxy groups having 1 to 4 carbon atoms, more preferably alkoxy groups;

Z represents $COOR_1$ or an aromatic ring, preferably $COOR_1$,

R represents the residue obtained by removing the isocyanate groups from an organic monomeric polyisocyanate or a polyisocyanate adduct, $R_1$ and $R_2$ are identical or different and represent organic groups which are inert to isocyanate groups at a temperature of 100° C. or less, preferably alkyl groups having 1 to 9 carbon atoms, more preferably methyl, ethyl or butyl groups $R_3$ and $R_4$ are identical or different and represent hydrogen or organic groups which are inert towards isocyanate groups at a temperature of 100° C. or less, preferably hydrogen and n is an integer from 1 to 8, preferably 2 to 4 and more preferably 3.

Especially preferred are compounds in which X represents methoxy, ethoxy groups or propoxy groups, more preferably methoxy or ethoxy groups and most preferably methoxy groups, and n is 3.

Examples of suitable aminoalkyl alkoxysilanes of formula III include 2-aminoethyl-dimethylmethoxysilane; 6-aminohexyl-tributoxysilane; 3-aminopropyl-trimethoxysilane; 3-aminopropyl-triethoxysilane; 3-aminopropyl-methyldiethoxysilane; 5-aminopentyl-trimethoxysilane; 5-aminopentyl-triethoxysilane and 3-aminopropyl-triisopropoxysilane. 3-aminopropyl-trimethoxysilane and 3-aminopropyl-triethoxysilane are particularly preferred.

Examples of optionally substituted maleic, fumaric or cinnamic acid esters suitable for use in the preparation of the polyaspartates include dimethyl, diethyl, dibutyl (e.g., di-n-butyl), diamyl, di-2-ethylhexyl esters and mixed esters based on mixture of these and/or other alkyl groups of maleic acid and fumaric acid; the methyl, ethyl and butyl esters of cinnamic acid; and the corresponding maleic, fumaric and cinnamic acid esters substituted by methyl in the 2- and/or 3-position. The dimethyl esters of maleic acid are preferred and the diethyl and dibutyl esters are especially preferred.

The reaction of primary amines with maleic, fumaric or cinnamic acid esters to form the aspartates of formula III is known and described, e.g. in EP-A-0,403,921; DE-OS 1,670,812; and DE-OS 2,158,945. While none of these publications suggests the reaction of alkoxysilane-functional amines with maleic or fumaric acid esters, this reaction is described in U.S. Pat. No. 5,364,955. The preparation of the aspartates may be carried out, for example, at a temperature of 0 to 100° C. using the starting materials in such proportions that at least 1, preferably 1, olefinic double bond is present for each primary amino group. Excess starting materials may be removed by distillation after the reaction. The reaction may be carried out with or without a solvent, but the use of a solvent is less preferred. If a solvent is used, dioxane is an example of a suitable solvent.

The compounds of formula II are colorless to pale yellow. They may be reacted with polyisocyanate monomer and/or adducts to form the compounds of formula I without further purification.

Suitable polyisocyanates for preparing the compounds of formula I are those having a functionality of 1.8 to 6, preferably 2 to 6 and more preferably 2 to 4. Suitable polyisocyanate starting materials include monomeric diisocyanates and polyisocyanate adducts.

Suitable monomeric diisocyanates may be represented by the formula

in which R represents an organic group obtained by removing the isocyanate groups from an organic diisocyanate having a molecular weight of about 112 to 1,000, preferably about 140 to 400. Diisocyanates preferred for the process according to the invention are those in which R represents a divalent aliphatic hydrocarbon group having 4 to 40, preferably 4 to 18 carbon atoms, a divalent cycloaliphatic hydrocarbon group having 5 to 15 carbon atoms, a divalent araliphatic hydrocarbon group having 7 to 15 carbon atoms or a divalent aromatic hydrocarbon group having 6 to 15 carbon atoms.

Examples of the suitable organic diisocyanates include 1,4-tetramethylene diisocyanate, 1,6-hexamethylene diisocyanate, 2,2,4-trimethyl-1,6-hexamethylene diisocyanate, 1,12-dodecamethylene diisocyanate, cyclohexane-1,3- and -1,4-diisocyanate, 1-isocyanato-2-isocyanatomethyl cyclopentane, 1-isocyanato-3-isocyanatomethyl- 3,5,5-trimethyl-cyclohexane (isophorone diisocyanate or IPDI), bis-(4-iso-cyanatocyclohexyl)-methane, 2,4'-dicyclohexyl-methane diisocyanate, 1,3- and 1,4-bis-(isocyanatomethyl)-cyclohexane, bis-(4-isocyanato-3-methyl-cyclohexyl)-methane, α,α,α',α'-tetramethyl-1,3- and/or -1,4-xylylene diisocyanate, 1-isocyanato-1-methyl-4 (3)-isocyanatomethyl cyclohexane, 2,4- and/or 2,6-hexahydrotoluylene diisocyanate, 1,3-and/or 1,4-phenylene diisocyanate, 2,4- and/or 2,6-toluylene diisocyanate, 2,4- and/or 4,4'-diphenyl-methane diisocyanate, 1,5-diisocyanato naphthalene and mixtures thereof.

Polyisocyanates containing 3 or more isocyanate groups such as 4-isocyanantomethyl-1,8-octamethylene diisocyanate and aromatic polyisocyanates such as 4,4',4"-triphenylmethane triisocyanate and polyphenyl polymethylene polyisocyanates obtained by phosgenating aniline/formaldehyde condensates may also be used.

Preferred organic diisocyanates include 1,6-hexamethylene diisocyanate, 1-isocyanato-3-isocyanatomethyl-3,5,5-trimethyl-cyclohexane (isophorone diisocyanate or IPDI), bis-(4-isocyanato-cyclohexyl)-methane, 1-isocyanato-1-methyl4(3)-isocyanatomethyl cyclohexane, 2,4- and/or 2,6-toluylene diisocyanate, and 2,4- and/or 4,4'-diphenyl-methane diisocyanate.

In accordance with the present invention the polyisocyanate component may also be in the form of a polyisocyanate adduct. Suitable polyisocyanate adducts are those containing isocyanurate, uretdione, biuret, urethane, allophanate, carbodiimide and/or oxadiazine-trione groups. The polyisocyanates adducts have an average functionality of 2 to 6 and an NCO content of 5 to 30% by weight.

1) Isocyanurate group-containing polyisocyanates which may be prepared as set forth in DE-PS 2,616,416, EP-OS 3,765, EP-OS 10,589, EP-OS 47,452, US-PS 4,288,586 and US-PS 4,324,879. The isocyanato-isocyanurates generally have an average NCO functionality of 3 to 3.5 and an NCO content of 5 to 30%, preferably 10 to 25% and most preferably 15 to 25% by weight.

2) Uretdione diisocyanates which may be prepared by oligomerizing a portion of the isocyanate groups of a diisocyanate in the presence of a suitable catalyst, e.g, a trialkyl phosphine catalyst, and which may be used in admixture with other aliphatic and/or cycloaliphatic polyisocyanates, particularly the isocyanurate group-containing polyisocyanates set forth under (1) above.

3) Biuret group-containing polyisocyanates which may be prepared according to the processes disclosed in U.S. Pat. Nos. 3,124,605; 3,358,010; 3,644,490; 3,862,973; 3,906,126; 3,903,127; 4,051,165; 4,147,714; or 4,220,749 by using co-reactants such as water, tertiary alcohols, primary and secondary monoamines, and primary and/or secondary diamines. These polyisocyanates preferably have an NCO content of 18 to 22% by weight and an average NCO functionality of 3 to 3.5.

4) Urethane group-containing polyisocyanates which may be prepared in accordance with the process disclosed in U.S. Pat. No. 3,183,112 by reacting excess quantities of polyisocyanates, preferably diisocyanates, with low molecular weight glycols and polyols having molecular weights of less than 400, such as trimethylol propane, glycerine, 1,2-dihydroxy propane and mixtures thereof. The urethane group-containing polyisocyanates have a most preferred NCO content of 12 to 20% by weight and an (average) NCO functionality of 2.5 to 3.

5) Allophanate group-containing polyisocyanates which may be prepared according to the processes disclosed in U.S. Pat. Nos. 3,769,318, 4,160,080 and 4,177,342. The allophanate group-containing polyisocyanates have a most preferred NCO content of 12 to 21% by weight and an (average) NCO functionality of 2 to 4.5.

6) Isocyanurate and allophanate group-containing polyisocyanates which may be prepared in accordance with the processes set forth in U.S. Pat. Nos. 5,124,427, 5,208,334 and 5,235,018, the disclosures of which are herein incorporated by reference, preferably polyisocyanates containing these groups in a ratio of monoisocyanurate groups to monoallophanate groups of about 10:1 to 1:10, preferably about 5:1 to 1:7.

7) Carbodiimide group-containing polyisocyanates which may be prepared by oligomerizing di- or polyisocyanates in the presence of known carbodiimidization catalysts as described in DE-PS 1,092,007, US-PS 3,152,162 and DE-OS 2,504,400, 2,537,685 and 2,552,350.

8) Polyisocyanates containing oxadiazinetrione groups and containing the reaction product of two moles of a diisocyanate and one mole of carbon dioxide.

Preferred polyisocyanate adducts are the polyisocyanates containing isocyanurate groups, biuret groups, allophanate groups and/or uretdione groups.

The compounds of formula I containing alkoxysilane groups and hydantoin groups are prepared by reacting the polyisocyanate monomers and/or adducts with the compounds of formula II at an equivalent ratio of aspartate groups (i.e., secondary amino groups) to isocyanate groups of approximately 1:1. The reaction is preferably carried out by incrementally adding the aspartate to the polyisocyanate. The reaction to form the urea groups is conducted at a temperature of 10 to 100° C., preferably 20 to 80° C. and more preferably 20 to 50° C.

The compounds of the present invention are suitable for the production of sealant (including caulks), coating or adhesive compositions which can be cross-linked by "silane polycondensation," i.e., the condensation of silane groups (Si—OR) to form siloxane groups (Si—O—Si). When used for this purpose, these compounds may be used as mixtures with suitable acidic or basic catalysts. Examples include acids such as paratoluene sulfonic acid; metallic salts such as dibutyl tin dilaurate; tertiary amines such as triethylamine or triethylene diamine; and mixtures of these catalysts. Low molecular weight, basic aminoalkyl trialkoxysilanes, such as those represented by formula IV, also accelerate hardening of the compounds according to the invention.

The invention is further illustrated but is not intended to be limited by the following examples in which all parts and percentages are by weight unless otherwise specified.

EXAMPLES

Polyisocyanate 1

An isocyanurate group-containing polyisocyanate prepared from 1,6-hexamethylene diisocyanate and having an isocyanate content of 21.6%, a content of monomeric diisocyanate of <0.2% and a viscosity at 20° C. of 3000 mpa.s (available from Bayer Corporation as Desmodur N 3300).

Polyisocyanate 2

A mixture containing 70 parts by weight of a uretdione group-containing polyisocyanate, i.e., dimerized 1,6-hexamethylene diisocyanate and 30 parts by weight of N,N',N"-tris-(6-isocyanatohexyl)-isocyanurate together with minor quantities of higher homologs of both products and having a average viscosity of 150 mPa.s at 23° C. and an average NCO content of 22.5% (available from Bayer Corporation as Desmodur N 3400).

Polyisocvanate 3

An aniline/formaldehyde condensation product containing a mixture of diphenylmethane diisocyanate isomers as well as their higher homologs, having an NCO content of about 31% and a viscosity of about 40 mpa.s at 23° C. (available from Bayer Corporation as Mondur MRS-4).

Polyisocyanate 4

87.5 parts (1 equiv) of a mixture of 2,4- and 2,6-toluylene diisocyanate (80:20 isomer ratio) was combined with 22.5 parts of 1,4-butanediol (0.5 equiv) in a round bottom flask. The reaction mixture was heated to 60° C. and held at that temperature until the % NCO reached 19.1.

Polyisocyanate 5

87.5 parts (1 equiv) of a mixture of 2,4- and 2,6-toluylene diisocyanate (80:20 isomer ratio) was combined with 33.5 parts of 1,4-butanediol (0.5 equiv) in a round bottom flask. The reaction mixture was heated to 60° C. and held at that temperature until the % NCO reached 17.4.

Polyisocyanate 6

A urethane group-containing polyisocyanate based on toluene diisocyanate and trimethylol propane; having an isocyanate content of 13.0%, a content of monomeric diisocyanate of <0.5% and a viscosity at 20° C. of about 1000 mPa.s; and present as a 75% solution in ethyl acetate (available from Bayer Corporation as Desmodur CB-75.

Preparation of N-(3-triethoxysilylpropyl) aspartic acid diethyl ester 8.27 equiv of 3-aminopropyltrialkoxysilane were added to a 5 liter flask fitted with agitator, thermocouple, nitrogen inlet and addition funnel with condenser. 8.27 equiv of diethyl maleate were added dropwise over a period of 2 hours. The temperature of the reactor was maintained at 25° C. during the addition. The reactor was maintained at 25° C. for an additional 5 hours at which time the product was poured into glass containers and sealed under a blanket of nitrogen. After one week the unsaturation number was 0.6 indicating the reaction was ~99% complete.

| The following compounds were prepared: | Viscosity at 25° C. |
|---|---|
| N-(3-trimethoxysilylpropyl) aspartic acid diethyl ester | 11 mPa · s |
| N-(3-triethoxysilylpropyl) aspartic acid dibutyl ester | 11 mPa · s |
| N-(3-trimethoxysilylpropyl) aspartic acid dibutyl ester | 18 mPa · s |

Alkoxysilane Resin 1

Tris-[3-(trimethoxysilyl)propyl]-isocyanurate (Silquest Y-11597, available from Witco Corp.).

Example 1

669.0 parts (1.7 equiv) of N-(3-trimethoxysilylpropyl) aspartic acid diethyl ester and 331 parts (1.7 equiv) of polyisocyanate 1 were added to a three neck, 5 liter, round bottom flask equipped with an agitator, nitrogen inlet, thermocouple and condenser. The reaction to form the urea was accompanied by an exotherm which increased the temperature of the reaction mixture to 80° C. The reaction was held at 80° C. for 14 hours at which time the IR spectrum showed no residual isocyanate in the urea. The product was cooled and the viscosity of the product was determined to be >300,000 at 25° C.

Analysis via GC, IR, NMR and GPC were consistent with the following structure:

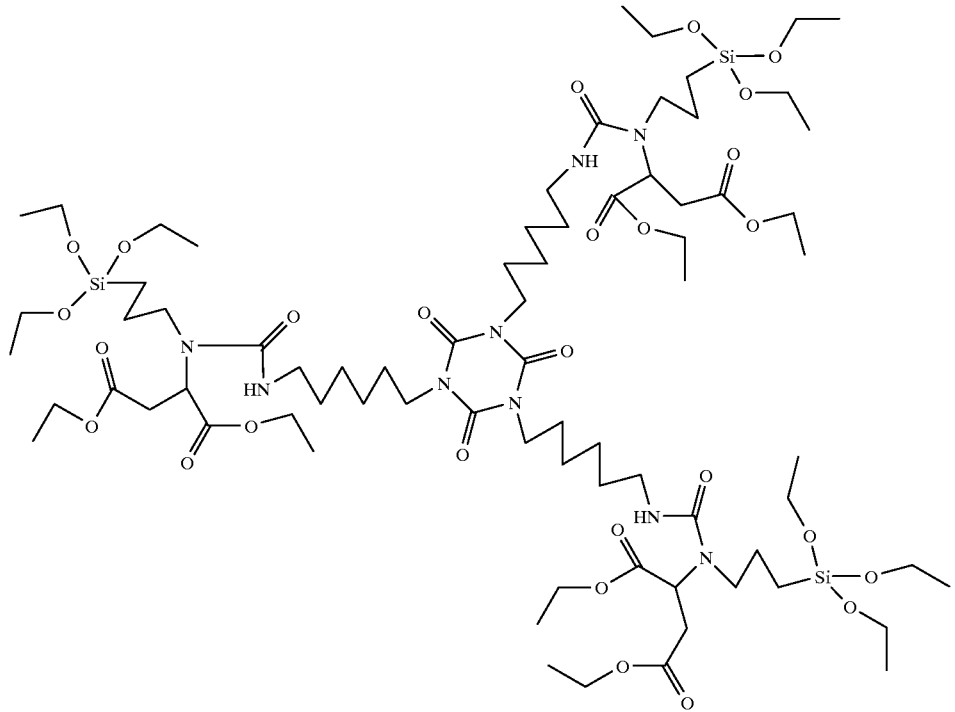

The product was seperately mixed with n-butyl acetate and xylene to form solutions having solids contents of 90%, 80% and 70%. The viscosities of these solutions are set forth in Table 1.

TABLE 1

| Solids content (%) | Solvent | Viscosity at 25° C. (mPa · s) |
|---|---|---|
| 100 | — | >300,000 |
| 90 | n-butyl acetate | 11,470 |
| 80 | n-butyl acetate | 2123 |
| 70 | n-butyl acetate | 492 |
| 90 | xylene | 13,760 |
| 80 | xylene | 1311 |
| 70 | xylene | 234 |

The product was also soluble in toluene and tetrahydrofuran.

Examples 2–18

Example 1 was repeated with the exception that Polyisocyanate 1 was replaced with an equivalent amount of polyisocyanates 2–7 and also with 1,6-hexamethylene diisocyanate (HDI), isophorone diisocyanate (IPDI) and bis-(4-isocyanatocyclohexyl)-methane (HMDI). In Example 11 an additional 100 g of propylene glycol methyl ether acetate was added to lower the viscosity of the reaction mixture. All of the resulting products were liquid and, more importantly, were soluble in toluene, xylene, butyl acetate and tetrahydrofuran.

In the comparison examples all of the preceding examples were repeated with the exception that each of the polyisocyanates was directly reacted with 3-aminopropyltrialkoxysilane instead of the aspartate of this silane. In every comparison example (except for comparison example 4) the resulting urea product solidified to form an entrained mixture of solvent and product. The product from comparison example 4 was an extremely high viscosity oil. In contrast to the examples according to the invention, the products of the comparison examples, including the product of comparison example 4, were not soluble in toluene, xylene, butyl acetate or tetrahydrofuran. Because the silane functional ureas could not be dissolved, they could not be used to prepare coatings.

The results are set forth in Table 2.

TABLE 2

| Example No. | Polyisocyanate | Viscosity of Urea at 25° C. (mPa · s) |
|---|---|---|
| 1 | Polyisocyanate 1 | >300,000 |
| 2 (Comp) | Polyisocyanate 1 | Insoluble Solid* |
| 3 | Polyisocyanate 2 | 21,600 |
| 4 (Comp) | Polyisocyanate 2 | Highly Viscous Oil* |
| 5 | Polyisocyanate 3 | 251,000 |
| 6 (Comp) | Polyisocyanate 3 | Insoluble Solid* |
| 7 | Polyisocyanate 4 | >300,000 |
| 8 (Comp) | Polyisocyanate 4 | Insoluble Solid* |
| 9 | Polyisocyanate 5 | >300,000 |
| 10 (Comp) | Polyisocyanate 5 | Insoluble Solid* |
| 11 | Polyisocyanate 6 | >300,000 |
| 12 (Comp) | Polyisocyanate 6 | Insoluble Solid* |
| 13 | HDI | 8200 |
| 14 (Comp) | HDI | Insoluble Solid* |
| 15 | IPDI | 160,000 |
| 16 (Comp) | IPDI | Insoluble Solid* |
| 17 | HMDI | 324,000 |
| 18 (Comp) | HMDI | Insoluble Solid* |

*These products could not be dissolved in xylene, toluene, butyl acetate or tetrahydrofuran.

Examples 19–22

Polyisocyanate 1 and HDI were each reacted with N-(3-triethoxysilylpropyl) aspartic acid dibutyl ester and N-(3-trimethoxysilylpropyl) aspartic acid dibutyl ester following the procedure of Example 1. All of the resulting products were liquid and soluble in toluene, xylene, butyl acetate and tetrahydrofuran. The results are set forth in the Table 3.

TABLE 3

| Example No. | Polyisocyanate | Trialkoxy Silane Aspartate | Viscosity of Urea at 25° C. (mPa · s) |
|---|---|---|---|
| 19 | Polyisocyanate 1 | Ethoxy | 80,300 |
| 20 | Polyisocyanate 1 | Methoxy | 158,000 |
| 21 | HDI | Ethoxy | 2200 |
| 22 | HDI | Methoxy | 3100 |

Example 23

Comparison

A coating composition was prepared by adding 1 part of dibutyl tin dilaurate to 100 parts (70% solids) of alkoxysilane resin 1, dissolved at 70% solids in toluene. The compositions were applied to steel panels at a wet film thickness of 5 mils (3.5 mils dry film thickness). The film cured with a cracked surface, was very friable and had no adhesion to the substrate.

Examples 24–25

Preparation of coatings from the urea group-containing compound of Example 1

Coatings were prepared from the urea group-containing compound prepared in Example 1. In addition to these compounds the coating compositions contained the ingredients set forth in Table 3. The levelling agent was Byk 358, a silicone based additive, available form Byk Chemie; the catalyst was dibutyl tin dilaurate. The properties of the resulting coatings are also set forth in Table 4.

TABLE 4

| Example | 24 | 25 |
|---|---|---|
| Ingredient | | |
| Urea from Ex. 1 | 200 | 100 |
| Alkoxysilane Resin 1 | 0 | 100 |
| Ethanol | 200 | 200 |
| Levelling Agent | 1 | 1 |
| Catalyst | 2 | 2 |
| Pendulum Hardness, sec. | | |
| Day  1 | 0 | 0 |
| 4 | 13 | 61 |
| 10 | 39 | 123 |
| 26 | 178 | 193 |
| Pencil Hardness, Day 26 | 2B | 3H |
| MEK Double Rubs | | |
| Day  1 | wet | wet |
| 4 | 1 | 70 |
| 10 | 25 | 100 |
| 26 | 100 | 100 |
| Chemical Spot Test: 1, 4 and 24 hour spots | | |
| Gasoline | ne,s,s | ne,ne,ne |
| Motor oil | ne,ne,ne | ne,ne,ne |
| Methyl ethyl ketone | ds,ds,ds, | ne,ne,ne |
| Isopropanol | s,s,s | ne,ne,ne |
| Propylene glycol methyl ether acetate | s,s,ds | ne,ne,ne |
| HCl, 37% | ne,st,bl | ne,st,ds |
| H$_2$SO$_4$, 50% | ne,ne,ne | ne,ne,st |
| Acetic acid | ds,ds,ds | s,ds,ds |
| Aniline | ds,ds,ds | ne,ne,ne |
| Tg, ° C. | 59 | 61 |

This example demonstrates the ability of compounds containing urea and alkoxysilane groups according to the invention to flexibilize other silane containing compounds that are not capable of forming films on their own. See comparison example 23.

MEK double rubs was determined by wetting a cloth with methyl ethyl ketone and then rubbing each panel up to 100 times. A double rub consists of one back and forth rub against the coated panel. Values of less than 100 indicate the number of double rubs before the coatings was destroyed.

Pendulum hardness was determined in accordance with ASTM D-4366-87 (Koenig Pendulum Hardness).

Chemical spot resistance was determined by placing a drop of the particular liquid on a coated panel and covering it with a 4 oz. glass jar. For those solvents that rapidly evaporate a cotton ball was placed on the coated panel liquids and kept saturated. After the appropriate time interval, the coated panels were washed, evaluated to determine the effect of the liquid, and assigned one of the following classifications:

| | |
|---|---|
| ne | No effect |
| s | Film softened, but recovered after 1 hour |
| ds | Dissolved |
| st | Stained |
| bl | Blistered |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. The present invention relates to compounds containing alkoxysilane and urea groups corresponding to the formula

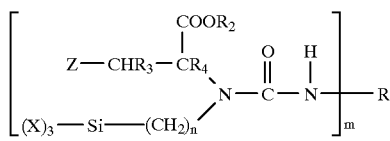 (I)

wherein
X represents identical or different organic groups which are inert to isocyanate groups below 100° C., provided that at least one of these groups is an alkoxy group,
Z represents $COOR_1$ or an aromatic ring,
R represents the residue obtained by removing the isocyanate groups from an organic monomeric polyisocyanate or a polyisocyanate adduct,
$R_1$ and $R_2$ are identical or different and represent organic groups which are inert to isocyanate groups at a temperature of 100° C. or less, $R_3$ and $R_4$ are identical or different and represent hydrogen or organic groups which are inert to isocyanate groups at a temperature of 100° C. or less and,
n is an integer from 1 to 8,
m is 1.8 to 6.

2. The compound of claim 1 wherein
X represents identical or different alkyl or alkoxy groups having 1 to 4 carbon atoms,
Z represents $COOR_1$,
$R_1$ is an alkyl group having 1 to 9 carbon atoms,
$R_3$ and $R_4$ represent hydrogen and
n is an integer from 2 to 4.

3. The compound of claim 1 wherein
X represents identical or different alkoxy groups having 1 to 4 carbon atoms,
Z represents $COOR_1$,
$R_1$ is methyl, ethyl or butyl,
$R_3$ and $R_4$ represent hydrogen and
n is 3.

4. The compound of claim 1 wherein R represents the residue obtained by removing the isocyanate groups from an organic monomeric polyisocyanate.

5. The compound of claim 2 wherein R represents the residue obtained by removing the isocyanate groups from an organic monomeric polyisocyanate.

6. The compound of claim 3 wherein R represents the residue obtained by removing the isocyanate groups from an organic monomeric polyisocyanate.

7. The compound of claim 1 wherein R represents the residue obtained by removing the isocyanate groups from a polyisocyanate adduct.

8. The compound of claim 2 wherein R represents the residue obtained by removing the isocyanate groups from a polyisocyanate adduct.

9. The compound of claim 3 wherein R represents the residue obtained by removing the isocyanate groups from a polyisocyanate adduct.

10. The compound of claim 1 wherein R represents the residue obtained by removing the isocyanate groups from a polyisocyanate adduct containing isocyanurate groups, biuret groups, allophanate groups and/or uretdione groups.

11. The compound of claim 2 wherein R represents the residue obtained by removing the isocyanate groups from a polyisocyanate adduct containing isocyanurate groups, biuret groups, allophanate groups and/or uretdione groups.

12. The compound of claim 3 wherein R represents the residue obtained by removing the isocyanate groups from a polyisocyanate adduct containing isocyanurate groups, biuret groups, allophanate groups and/or uretdione groups.

13. A coating, sealant or adhesive prepared from the compounds of claim 1.

* * * * *